(12) United States Patent
Patterson et al.

(10) Patent No.: US 7,427,297 B2
(45) Date of Patent: Sep. 23, 2008

(54) PROSTHETIC SOCKET WITH SELF-CONTAINED VACUUM RESERVOIR

(75) Inventors: William Stan Patterson, Orlando, FL (US); William E. Patterson, Titusville, FL (US)

(73) Assignee: Ossur HF, Reykjavik (IS)

( * ) Notice: Subject to any disclaimer, the term of this patent is extended or adjusted under 35 U.S.C. 154(b) by 669 days.

(21) Appl. No.: 10/869,915

(22) Filed: Jun. 18, 2004

(65) Prior Publication Data

US 2004/0260403 A1    Dec. 23, 2004

Related U.S. Application Data

(60) Provisional application No. 60/480,350, filed on Jun. 20, 2003.

(51) Int. Cl.
*A61F 2/80* (2006.01)
(52) U.S. Cl. .......................................................... 623/34
(58) Field of Classification Search .................... 623/34
See application file for complete search history.

(56) References Cited

U.S. PATENT DOCUMENTS

| | | | |
|---|---|---|---|
| 1,398,824 A | 11/1921 | Abrams | |
| 2,530,285 A * | 11/1950 | Catranis | 623/44 |
| 2,533,404 A | 12/1950 | Sharp et al. | |
| 2,671,225 A | 3/1954 | Schoene et al. | |
| 2,808,593 A | 10/1957 | Andersen | |
| 3,393,407 A | 7/1968 | Kandel | |
| 3,671,980 A | 6/1972 | Baird | |
| 5,007,937 A | 4/1991 | Fishman et al. | 623/34 |
| 5,139,523 A | 8/1992 | Paton et al. | 623/37 |
| 5,163,965 A | 11/1992 | Rasmusson et al. | 623/36 |
| 5,226,918 A | 7/1993 | Silagy et al. | 623/32 |
| 5,376,129 A | 12/1994 | Faulkner et al. | 623/33 |
| 5,658,353 A | 8/1997 | Layton | 623/34 |
| 5,702,489 A | 12/1997 | Slemker | 623/34 |
| 5,718,925 A | 2/1998 | Kristinsson et al. | 425/2 |
| 5,728,170 A | 3/1998 | Becker et al. | 623/37 |
| 5,735,906 A | 4/1998 | Caspers | 623/34 |
| 5,888,216 A | 3/1999 | Haberman | 623/36 |
| 5,904,722 A | 5/1999 | Caspers | 623/34 |
| 5,931,872 A | 8/1999 | Lohmann | 623/36 |
| 5,972,036 A | 10/1999 | Kristinsson et al. | 623/33 |
| 6,149,691 A | 11/2000 | Fay et al. | 623/37 |
| 6,231,616 B1 | 5/2001 | Helmy | 623/34 |

(Continued)

FOREIGN PATENT DOCUMENTS

DE    745 981    12/1943

(Continued)

*Primary Examiner*—David Willse
(74) *Attorney, Agent, or Firm*—Bacon & Thomas, PLLC

(57) ABSTRACT

A prosthetic socket having a self-contained vacuum reservoir chamber includes a rigid, load-bearing inner socket member for receiving a residual limb and an outer, rigid, load-bearing wall section attached to the inner wall section in a manner providing a vacuum reservoir chamber between the inner wall and the outer wall section. The vacuum reservoir chamber communicates with the inner volume of the inner wall through a vacuum transfer port and the vacuum reservoir chamber may be evacuated via an evacuation port having an appropriate one-way check valve permitting withdrawal of air from the vacuum reservoir chamber while preventing ingress of air into the chamber. A method for making the prosthetic socket is disclosed.

29 Claims, 5 Drawing Sheets

U.S. PATENT DOCUMENTS

| | | | |
|---|---|---|---|
| 6,273,918 B1 | 8/2001 | Yuhasz et al. | 623/33 |
| 6,287,345 B1 | 9/2001 | Slemker et al. | 623/34 |
| 6,361,568 B1 | 3/2002 | Hoerner | 623/32 |
| 6,508,842 B1 | 1/2003 | Caspers | 623/32 |
| 6,554,868 B1 | 4/2003 | Caspers | 623/34 |
| 6,585,774 B2 | 7/2003 | Dean, Jr. et al. | 623/37 |
| 6,645,253 B2 | 11/2003 | Caspers | 623/26 |
| 6,726,726 B2 | 4/2004 | Caspers | 623/34 |
| 6,761,742 B2 | 7/2004 | Caspers | 623/34 |
| 2001/0005798 A1 | 6/2001 | Caspers | 623/34 |
| 2001/0016781 A1 | 8/2001 | Caspers | 623/34 |
| 2002/0040248 A1 | 4/2002 | Karason | 623/37 |
| 2002/0087215 A1 | 7/2002 | Caspers | 623/34 |
| 2002/0091449 A1* | 7/2002 | Caspers et al. | 623/34 |
| 2002/0099450 A1 | 7/2002 | Dean, Jr. et al. | 623/26 |
| 2003/0191539 A1 | 10/2003 | Caspers | 623/35 |
| 2004/0030411 A1 | 2/2004 | Caspers | 623/37 |
| 2004/0098136 A1 | 5/2004 | Caspers | 623/34 |
| 2004/0143345 A1 | 7/2004 | Caspers | 623/36 |
| 2004/0167638 A1 | 8/2004 | Caspers | 623/27 |
| 2004/0181290 A1 | 9/2004 | Carstens | 623/34 |
| 2004/0236434 A1 | 11/2004 | Carstens | 623/34 |
| 2004/0243251 A1 | 12/2004 | Carstens | 623/34 |
| 2004/0243252 A1 | 12/2004 | Carstens | 623/34 |

FOREIGN PATENT DOCUMENTS

| | | |
|---|---|---|
| DE | 813190 | 7/1951 |
| DE | 1795809 | 9/1959 |
| DE | 2540138 | 3/1977 |
| DE | 3221920 | 4/1983 |
| DE | 3508919 | 9/1986 |
| DE | 9419208.1 | 11/1994 |
| GB | 267988 | 3/1927 |
| GB | 2 069 847 | 9/1981 |
| GB | 2 087 727 | 6/1982 |
| JP | 7155343 | 6/1995 |
| WO | 01/54631 A1 | 8/2001 |
| WO | 03/024367 A2 | 3/2003 |
| WO | 03/024370 A1 | 3/2003 |
| WO | 03/039398 A2 | 5/2003 |
| WO | 03/099173 A1 | 12/2003 |

* cited by examiner

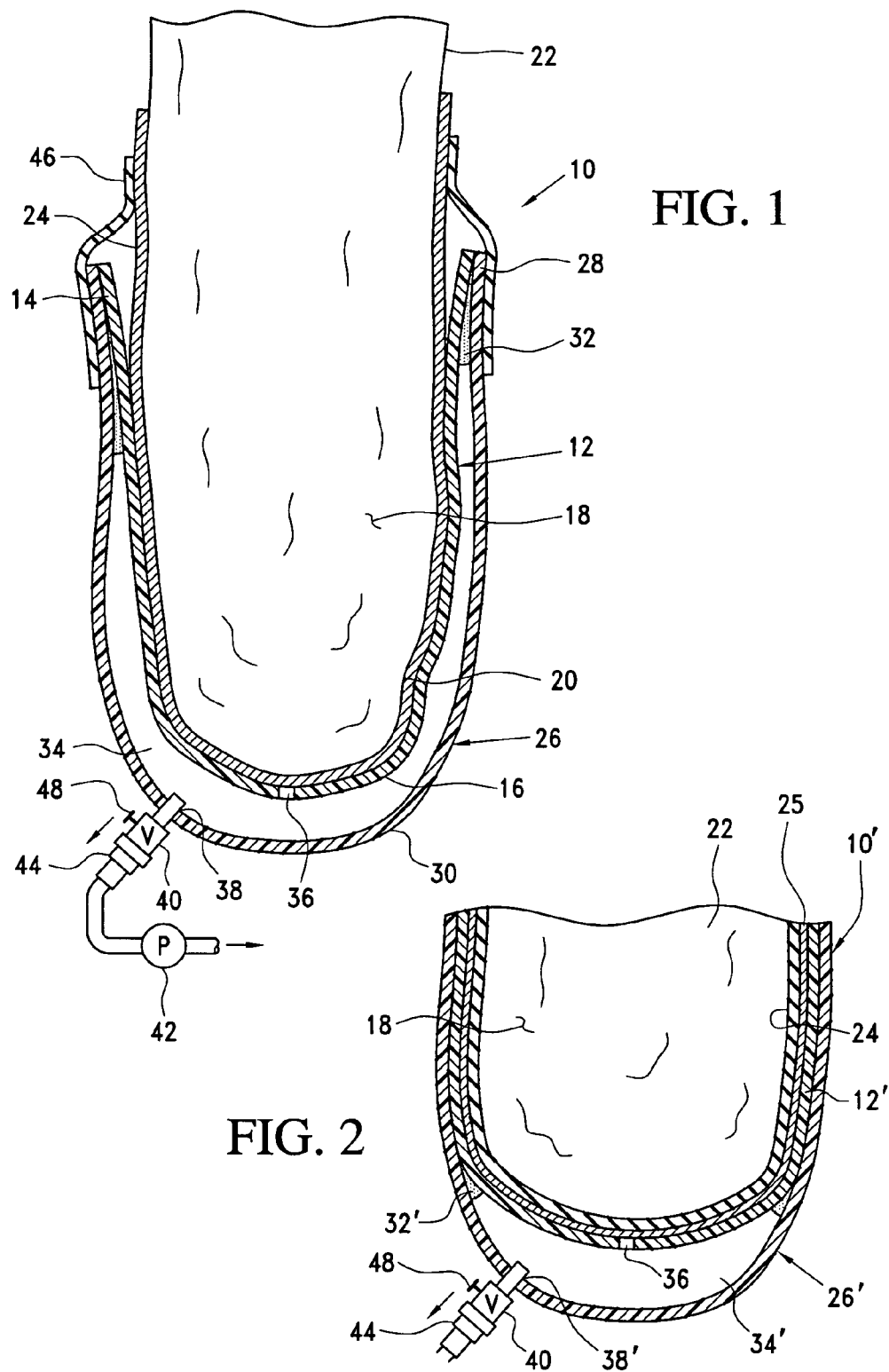

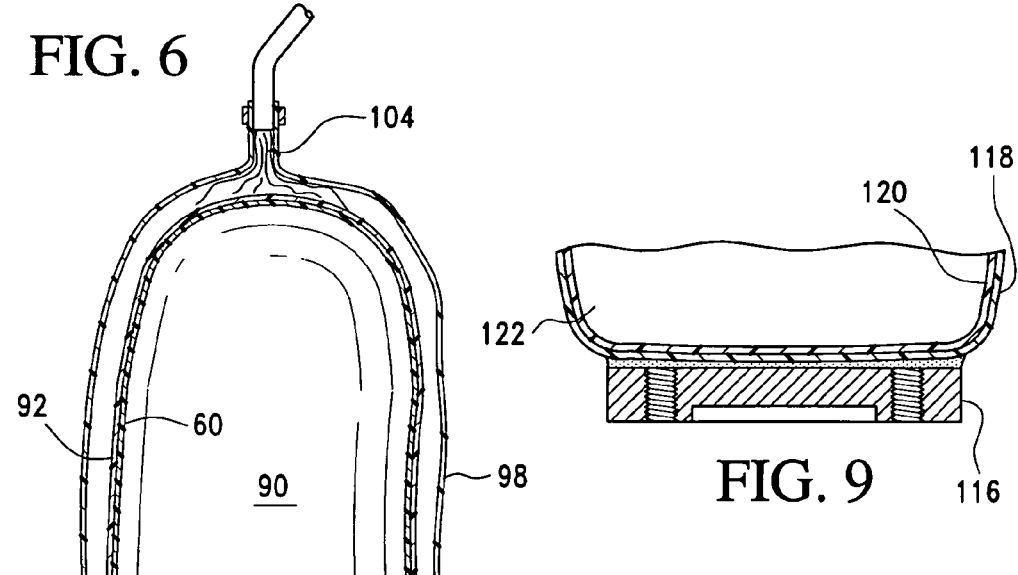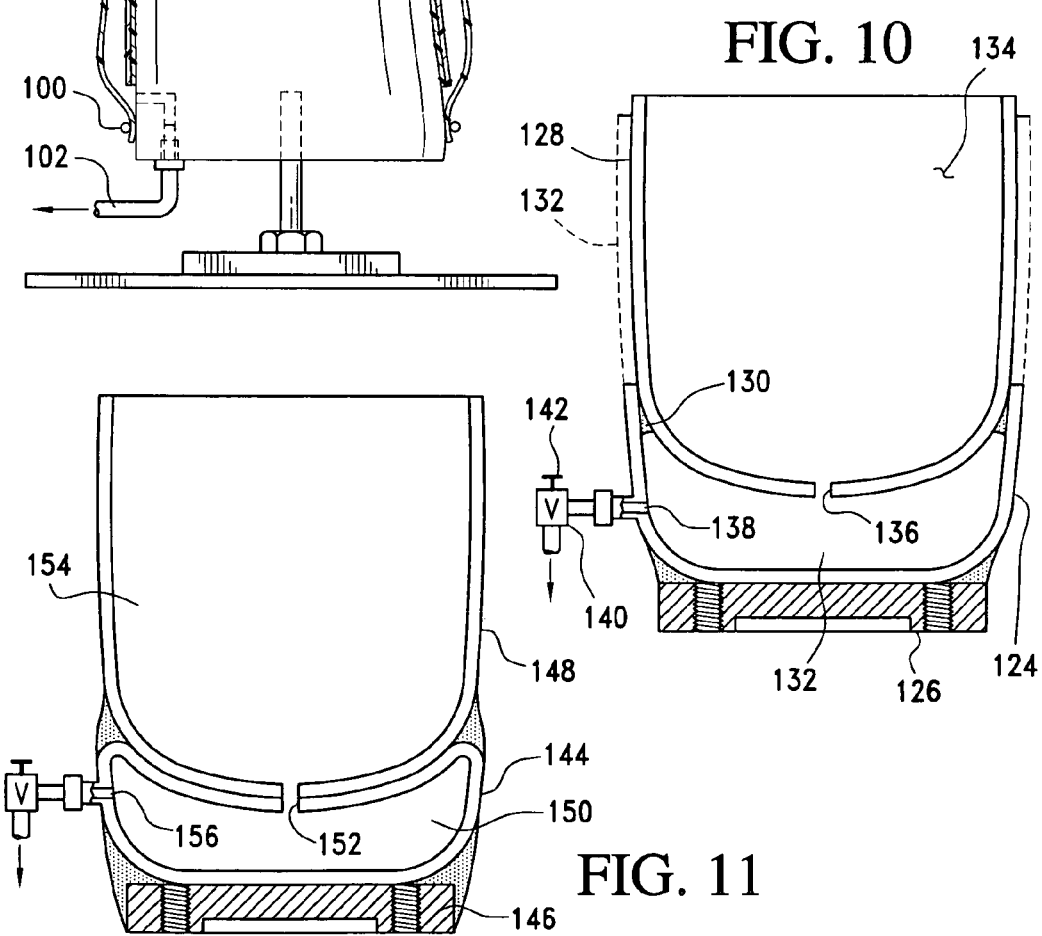

PROSTHETIC SOCKET WITH SELF-CONTAINED VACUUM RESERVOIR

This application claims the benefit of U.S. provisional patent application No. 60/480,350 filed Jun. 20, 2003.

BACKGROUND OF THE INVENTION

1. Field of the Invention

This invention relates to vacuum suspension prosthetic sockets.

2. Discussion of Related Art

Amputees have retained prosthetic devices on their residual limbs using various vacuum or suction arrangements for many years, particularly since the advent of soft cushion liners that are worn between the residual limb and the prosthetic socket. Typically, a one-way valve is provided at a distal end of an otherwise closed socket arranged to receive the distal end portion of a residual limb whereby air in front of the distal end of the residual limb may be exhausted until the residual limb and its donned liner are fully inserted into the socket.

The one-way valve thereafter is maintained in a closed condition and forces tending to separate the prosthetic socket from the residual limb are resisted by induced sub-atmospheric pressure between the distal end of the residual limb and the distal end of the socket.

It is necessary, of course, with vacuum suspensions to maintain the sub-atmospheric pressure or vacuum at the distal end of the socket and appropriate sealing sleeves and other arrangements are typically provided to prevent influx of air around the distal end of the residual limb and into the distal end of the socket. Obviously, with a vacuum suspension system, any significant loss of vacuum will result in separation of the prosthetic socket from the residual limb unless an additional element is provided to retain the socket attached to the residual limb.

It has been recognized in the prior art to provide a vacuum reservoir chamber maintained at sub-atmospheric pressure and in communication with a prosthetic socket for the purpose of maintaining an appropriate partial vacuum within the socket to compensate for variations in volume of the residual limb while the prosthetic socket is worn and to compensate for air leakage around the residual limb. U.S. published patent application No. U.S. 2001/0005798 A1 published Jun. 28, 2001 discloses a reservoir maintained at sub-atmospheric pressure mounted on a pylon of a prosthetic device and communicating with the interior of the prosthetic socket via a conduit connected to the reservoir. Such arrangements are unwieldy and tend to add to the weight of the prosthetic device suspended from the prosthetic socket. The added weight contributes to added inertia which would be noticeable to a leg amputee.

U.S. Pat. No. 2,530,285 issued Nov. 14, 1950 describes a chamber in the distal end area of a prosthetic socket that may be maintained at sub-atmospheric pressure, such chamber being integrated with the prosthetic socket, but having a movable diaphragm as a side wall of the chamber for the purpose of actuating a knee lock of a prosthetic device carried by the socket. This patent also shows the distal end of the residual limb extending into the chamber, so that the total effect of the diaphragm and the residual limb extending into the chamber is to produce a variable volume chamber as the diaphragm and the residual limb move during implementation of the prosthetic socket. The pressurization of the vacuum chamber in accordance with this patent is necessary to produce motion of the diaphragm to effect locking of the knee joint carried by the prosthetic socket. Movement of the prosthetic socket disclosed by this patent tending to separate the socket from the residual limb would result in deformation of the diaphragm in a reverse direction into the chamber thereby creating insecurity on the part of the amputee as to whether or not an appropriate vacuum was being maintained below the residual limb.

U.S. Pat. No. 2,671,225 describes a prosthetic socket having a flexible inner sac of soft, elastomeric resin permanently bonded to the interior of a hard outer, load bearing socket wherein a chamber at the end of the sac is provided between the distal end of a residual limb inserted into the sac and the distal wall of the sac, such chamber being in communication with a one-way valve that permits exhaust of air between the residual limb and the distal wall of the sac but does not permit air to enter the chamber. This form of suspension liner suffers from the problem that the sac itself is flexible and even though there is a vacuum maintained at the distal end of the sac, the sac itself can move relative to the outer socket due to its flexible characteristics. Thus, the chamber is not actually a reservoir, but merely a chamber from which air has been exhausted and into which the admittance of air is prevented in an attempt to create a vacuum suspension system.

U.S. Pat. No. 2,533,404 discloses a one-way exhaust valve at the distal end of a prosthetic socket for exhausting air between the distal end of a residual limb inserted into the socket and the disclosed distal wall of the socket. While the volume of the chamber at the distal end of the prosthetic socket is relatively fixed, nevertheless, there is no reservoir provided to compensate for any leakage of air into the chamber or to compensate for the varying volume of the residual limb within the prosthetic socket.

U.S. Pat. Nos. 5,702,489 and 6,287,345 granted respectively on Dec. 30, 1997 and Sep. 11, 2001 describe other approaches to vacuum suspension systems whereby a relatively pliable end wall element is inserted into the distal end of a rigid, load-bearing prosthetic socket and the end wall is provided with an air chamber integrated therein in communication with a valve arrangement and a quick-disconnect port via which gas may be sucked from the socket by means of apertures provided in the flexible cushion end wall. Obviously, in accordance with this construction, the distal end of a prosthetic limb bearing against the flexible end wall would have an effect on the volume of the chamber within the end wall within which a sub-atmospheric pressure has been established.

U.S. Pat. No. 6,231,616 issued May 15, 2001 describes a prosthetic socket including an arrangement for establishing a vacuum between a liner donned on a residual limb and the inner surface of a prosthetic socket.

German Patent No. 745981 issued on May 22, 1944 describes a suction suspension system for a prosthetic socket wherein leg motion of a prosthetic device actuates a suction pump that creates a vacuum between the distal end of a residual limb and the distal end wall of an outer socket.

U.S. Pat. No. 5,658,353 discloses another arrangement whereby a suction pump it utilized to create suction between the distal end of a residual limb and the inner wall of a socket arranged to receive the residual limb to facilitate insertion of the limb and to the socket.

Thus, it is evident that the use of suction to facilitate insertion of a residual limb into a load-bearing socket and the use of suction to maintain the residual limb within the socket is well-known in the prior art. What is obviously lacking in the prior art is a suitable arrangement for maintaining a sub-atmospheric pressure between the residual limb and the inner walls of a socket despite variations in volume of the residual limb and further despite minor air leakage around the residual limb tending to relieve the vacuum within the socket.

Ideally, a reservoir containing a volume of sub-atmospheric pressure integrated with a load-bearing socket would provide insurance against volume variations of a residual limb and minor air leakage into the socket. Such an arrangement furthermore would need to be light weight and smoothly integrated with a prosthetic socket so as not to unduly enlarge the outer profile of the socket. It would be highly desirable to provide a load-bearing prosthetic socket that may be readily coupled to a prosthetic device in a conventional manner while providing a vacuum reservoir chamber within the socket itself and without diminishing the strength and load bearing characteristics of the socket. It also would be highly desirable to provide such a vacuum chamber with rigid walls capable of maintaining a constant volume during implementation of the prosthetic socket containing the reservoir vacuum chamber.

BRIEF SUMMARY OF THE INVENTION

The present invention has for its objective, the provision of a prosthetic socket having an integrated vacuum reservoir chamber meeting the criteria discussed above.

In accordance with this invention, a prosthetic socket is provided with a rigid, structural, air impervious inner wall in the form of a close ended cup having an open inner wall proximal end and a closed inner wall distal end area, the inner wall defining an inner volume adapted to contain a distal portion of a residual limb and wherein the inner wall proximal end is adapted to receive a distal portion of a residual limb to be located within the inner volume. A generally cup-shaped, rigid, air impervious structural outer wall section having an outer wall section proximal end and a closed outer wall section distal end area is hermetically sealed to the inner wall to define a chamber located between the outer side of the inner wall and an inner side of the outer wall section wherein the chamber is hermetically sealed along the hermetic sealing connection. At least one aperture in the inner wall communicates with the inner volume of the inner wall with the chamber and a port is provided to provide communication between the chamber and an area external of the outer wall section. Thus, a partial vacuum may be established within the chamber via the port when a residual limb is contained in the inner volume of the inner wall and the partial vacuum may be communicated to the inner volume of the inner wall to effect a vacuum suspension of the prosthetic socket on a residual limb via the aperture in the inner wall.

The invention also constitutes providing a prosthetic socket adapted for vacuum suspension of a prosthetic device relative to a residual limb wherein the socket comprises a rigid, structural cup-shaped socket member defining a substantially closed distal end, an inner volume terminating distally at a distal end for receiving a distal portion of a residual limb, and an open proximal end arranged to admit a distal portion of a residual limb into the inner volume. A vacuum reservoir chamber located externally of and carried by the socket member is defined at least in part by a chamber wall section carried by the socket member externally of the socket member, such chamber wall section being sufficiently rigid and inflexible so as to avoid substantial deflection when the pressure in the reservoir chamber varies during implementation of the prosthetic socket. An evacuation port in communication with the reservoir chamber enables establishment of a partial vacuum within the reservoir chamber and at least one vacuum transfer port communicating the reservoir chamber with the inner volume of a the socket member is provided for enabling transfer of a partial vacuum within the reservoir chamber into the inner volume.

Preferably, the transfer port is substantially smaller in cross section than the closed distal end of the socket member.

The invention also relates to a method for forming a prosthetic socket of the kind described above having a rigid inner socket component and a rigid, load-bearing outer socket component by pre-forming at least one wall of a vacuum reservoir chamber and joining the wall with a load-bearing component to a rigid inner load-bearing socket member whereby a vacuum reservoir chamber is created within an outer, structurally rigid and load-bearing socket component that functions to transfer loads between a prosthetic device and the inner socket during implementation of the prosthetic socket system.

DESCRIPTION OF THE DRAWINGS

With reference to the appended drawings:

FIG. 1 is a vertical sectional view of a first embodiment of a prosthetic socket embodying the present invention;

FIG. 2 is a partial vertical sectional view of the distal end area of a prosthetic socket made in accordance with the invention;

FIG. 6 shows a step in a process for making a component of a prosthetic socket in accordance with the present invention;

FIG. 9 shows an alternate embodiment of the invention;

FIG. 10 shows another alternate embodiment of the invention; and

FIG. 11 shows another alternate embodiment of the invention.

DETAILED DESCRIPTION OF PREFERRED EMBODIMENTS OF THE INVENTION

Figure 3:
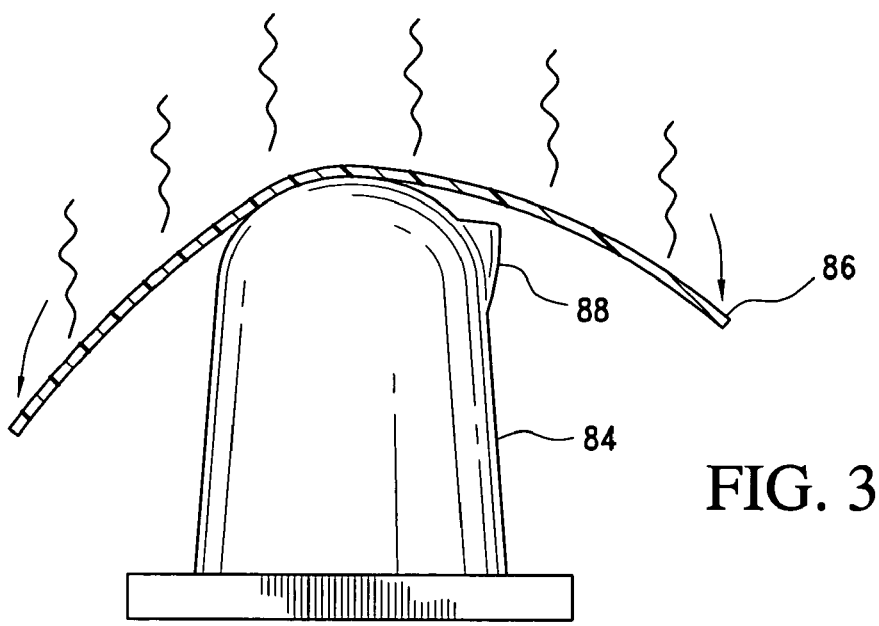
FIGS. 3 and 4 are schematic views illustrative of a process for making a component of a prosthetic socket in accordance with the present invention.

With reference to the appended views, preferred embodiments of the present invention are illustrated to provide exemplary examples of prosthetic sockets arranged to carry a vacuum reservoir chamber within the socket to provide a source of sub-atmospheric pressure in the socket sufficient to maintain the distal end portion of a residuum of an amputee within a rigid inner socket element member so that a partial vacuum may be maintained between the residuum and the inner rigid socket element member during implementation of the prosthetic socket constructed in accordance with the invention. By providing a sub-atmospheric or vacuum chamber reservoir within the socket assembly, the need for a separate vacuum reservoir chamber is eliminated along with a structural complexity, weight and conduits associated with an external vacuum reservoir.

With reference to FIG. 1, an example of a prosthetic socket 10 embodying the invention comprises an assembly of a rigid, structural, load bearing, air impervious inner wall 12 in the form of a close ended cup having an open inner wall proximal end 14 and a closed inner wall distal end area 16, the inner wall defining an inner volume 18 adapted to contain a distal portion 20 of a residual limb 22. The inner wall 12 defines an inner socket member. The proximal end 14 of the inner wall 12 is adapted to receive the distal end portion 20 of the residual limb within the inner volume 18. The inner wall 12 is constructed of a material having sufficient structural strength and rigidity to fully support the loads imposed by the residual limb 22 during implementation of the prosthetic socket 10. Preferably, the inner wall 12 is constructed of a resin-impregnated carbon fiber matrix of the type suitable for use in prosthetic appliances including prosthetic sockets.

Typically, a resilient, flexible suction liner 24 is donned on the residual limb 22, such suction liner commonly formed of a silicone elastomer, such suction liners being well known in the art.

Rigidly bonded to the inner wall 12 is an outer cup-shaped, rigid, structural, load bearing outer wall section 26 having an outer wall section proximal end 28 and a closed outer wall section distal end area 30. The outer wall section 26 is air impervious, is at least partially spaced from the inner wall section 12 and is rigidly bonded to the inner wall section 12 such as by the bonded connection 32 shown in this embodiment at the proximal ends of the inner wall 12 and the outer wall section 26. The volume 34 between the external surface of the inner wall 12 and the inner surface of outer wall section 26 defines a chamber 34 that is substantially hermetically sealed with the exception of an aperture or channel 36 providing a port enabling communication between the chamber 34 and the inner volume 18 of the inner wall 12 and an outlet or evacuation port 38 providing communication between the chamber 34 and an area external of the outer wall section 26. A one-way valve 40 preferably is provided so that it is in communication with outlet port 38 to enable withdrawal of air within chamber 34 via a pump 42 of any suitable type, including manual, electrical, fluid or mechanically energized, whereby a sub-atmospheric pressure may be established in reservoir chamber 34 by exhausting air from the chamber to an area external of the chamber. Following evacuation of chamber 34, the port 38 may be isolated from atmosphere by disconnecting the pump 42 from the one-way valve 40 by means of a disconnect 44 or in any suitable fashion that would be apparent to a person skilled in the art, whereby the port 38 effectively is isolated from atmosphere in a selective manner so that air trapped between the residual limb 22 and liner 24 may be discharged to the port 38 when the limb is inserted into the inner volume 18 via aperture 36 and one-way valve 40. After the distal end of the residual limb 22 is contained fully within the volume 18 in inner wall 12, a connection to the one-way valve 40 may be established between the valve and a pump 42 to enable withdrawal of air from chamber 34 to a sub-atmospheric pressure or partial vacuum that is communicated to the interior volume 18 of the inner wall 12 via the port aperture or channel 36.

Liner 24 typically is provided with a fabric or fabric-like surface (i.e., flocking or non-woven) on its outer periphery or in the form of a fabric sock that communicates the partial vacuum throughout the inner volume 18 towards the proximal end 14 of inner wall 12. A sealing sleeve 46 is provided to effect a seal between the outer surface of the outer wall section 26 and an end portion of the elastomeric liner 24 that is made without a fabric or other porous material to enable sealing directly against the elastomer and air impervious liner outer surface in accordance with the preferred embodiment.

The sealing sleeve 46 is constituted of an elastomeric material such as silicone and is donned over the proximal end of the outer wall section 26 by stretching the sleeve into conformity with the outer wall while the sleeve spans the gap between the proximal end 28 of the outer wall section 26 and the proximal end of the liner 24 in a hermetic relationship. Alternatively, the proximal end of the sealing sleeve 46 may engage the exterior of the residual limb 22 and the proximal end of the liner 24 will terminate below the proximal end of the sealing sleeve 46.

Thus, upon a disconnect of the pump and its associated conduit from one-way valve 40 via disconnect 44, the chamber 34 provides a reservoir of partial vacuum that is communicated via aperture or vacuum transfer port 36 to the interior volume 18 of inner wall 12 that is hermetically sealed by sealing sleeve 46, thereby ensuring maintenance of a partial vacuum within the inner volume 18. If any slight leakage would occur into the inner volume 18, the partial vacuum within reservoir 34 compensates for the leakage by maintaining a partial vacuum within the inner volume 18. In an extreme situation, of course, the chamber 34 no longer contains a partial vacuum sufficient to hold the distal limb 22 and its associated liner 24 within the inner wall 12.

A reservoir chamber 34 associated directly with the socket 10 and constituting a chamber within the socket 10 eliminates the need for an external vacuum reservoir for maintaining suction within the inner volume 18 against possible leakage into the inner volume.

A manual vacuum release 48 of any suitable form may be provided in association with one-way valve 40 to enable ventilation of vacuum chamber 34 with atmospheric pressure when it is desired to withdraw the residual limb 22 and its associated liner 24 from the inner volume 18 of the inner wall 12. Any appropriate suction relief device may be substituted for the suction relief element 48 associated with the valve 40, and such relief need not be directly associated with the valve 40 but may be provided as a separate element associated with chamber 34.

The volume between the inner wall 12 and outer wall section 26 need not extend in a proximal direction over the majority of the length of the inner wall 12, the only requirement being that the volume of the reservoir chamber 34 must be adequate to maintain a sub-atmospheric pressure within the chamber and the inner volume 18 for a reasonable period of time during implementation of the socket 10. Thus, as shown in FIG. 2, in an alternate embodiment of a prosthetic socket 10' according to the invention, the outer wall section 26' constituting a cup-shaped, rigid air impervious structural corresponding generally with the outer wall section 26 described above extends in contiguous relationship with the inner wall 12' corresponding with inner wall 12 described above with regard to the embodiments shown in FIG. 1 and is bonded thereto to provide a rigid laminated assembly of inner wall 12' and outer wall section 26'.

The distal end area of the outer wall section 26' is spaced from the distal end of the inner wall 12' to define a vacuum reservoir chamber 34' that is hermetically sealed relative to atmosphere apart from aperture 36 and port 38' communicating with one-way valve 40 in a manner similar to that described above with regard to the embodiment of the invention shown in FIG. 1.

In the embodiment of FIG. 2, the reservoir chamber 34' defines a smaller volume than the volume 34 illustrated in the embodiment shown in FIG. 1, but in each case the volume of the reservoir chambers 34, 34' would be adequate to maintain an adequate suction or negative pressure within inner volume 18 despite minor leakage of air into the inner volume 18.

The structure and strength of the inner wall 12 and the outer wall section 26 which together define inner and outer socket elements is sufficient to withstand the rigors and loads incidental to use of the prosthetic socket 10 for all normal applications. The structure of the inner wall 12 and the outer wall section 26 must be such that a volume of the reservoir chambers 34, 34' are substantially maintained. Thus, flexure of the inner wall 12 relative to the outer wall section 26' is to be avoided as much as possible or practical in the area between the inner wall 12, 12' and the outer wall section 26, 26' defining the vacuum reservoir chamber 34, 34'. Obviously, any substantial deflection of the walls 12, 12', 26, 26' tending to cause a collapse of the reservoir chambers 34, 34' would defeat the purpose of the invention namely the maintenance of a reservoir volume of sub-atmospheric pressure in a self-contained manner within a prosthetic socket sufficient to compensate for minor leakage of air into the inner volume of the socket containing a residual limb.

It will be noted that the vacuum transfer aperture or port 36 is shown as a single opening in the distal end of inner wall 12', such single aperture comprises a preferred embodiment of the invention. However, several apertures may be provided in the distal end of inner wall 12' to transfer suction from chamber 34, 34' to the inner volume 18. Such vacuum transfer aperture or apertures 36 are substantially smaller than the distal end area 16 of the inner wall 12 which receives and supports the distal end area of the residual limb 22 in a manner permitting the distal end of the residual limb to comfortably seat against the distal end area 16 of the inner wall 12. As noted previously, it is important that the volume of chamber 34, 34' be maintained after sub-atmospheric pressure has been established in the chambers and any intrusion of the distal end of residual limb 22 or the liner 24 into the chamber 34, 34' would adversely affect the volume of the chamber 34, 34'. It has been observed that a single vacuum transfer aperture 36 is adequate to transfer sub-atmospheric pressure within chamber 34 to inner volume 18 provided that a fabric covering or the equivalent is provided along the outer surface of the liner 24 to prevent sealing of the liner directly against the inner side of the inner wall 12.

It is to be noted that the provision of a sealing sleeve 46 to maintain a vacuum within the inner volume 18 constitutes a preferred embodiment of the invention but any sealing arrangement between the liner 24 and the inner surface of the inner wall 12 that would prevent admission of air into the space between the distal end of the residual limb 22 and the associated liner 24 would achieve the objective of maintaining suction at the distal end of the inner wall 12. The liner 24 in FIG. 2 includes a fabric covering 25 that facilitates distribution of suction forces over the distal area of the residual limb and its liner 24, but any appropriate force distribution scheme could be utilized to avoid intense concentration of suction at a single or very localized area of the residual limb. Indeed, a porous sock could also be used directly donned on the residual limb.

While the embodiment illustrated in FIGS. 1 and 2 do not show a prosthetic device associated with the prosthetic socket 10, 10', it will be understood that attachment of prosthetic devices to such sockets constitutes well-known technology known to those skilled in the art. An appropriate adaptor for connecting the socket 10, 10' to a prosthetic device is described below in connection with the embodiment of the invention illustrated in FIGS. 7-11 below.

Figure 8:
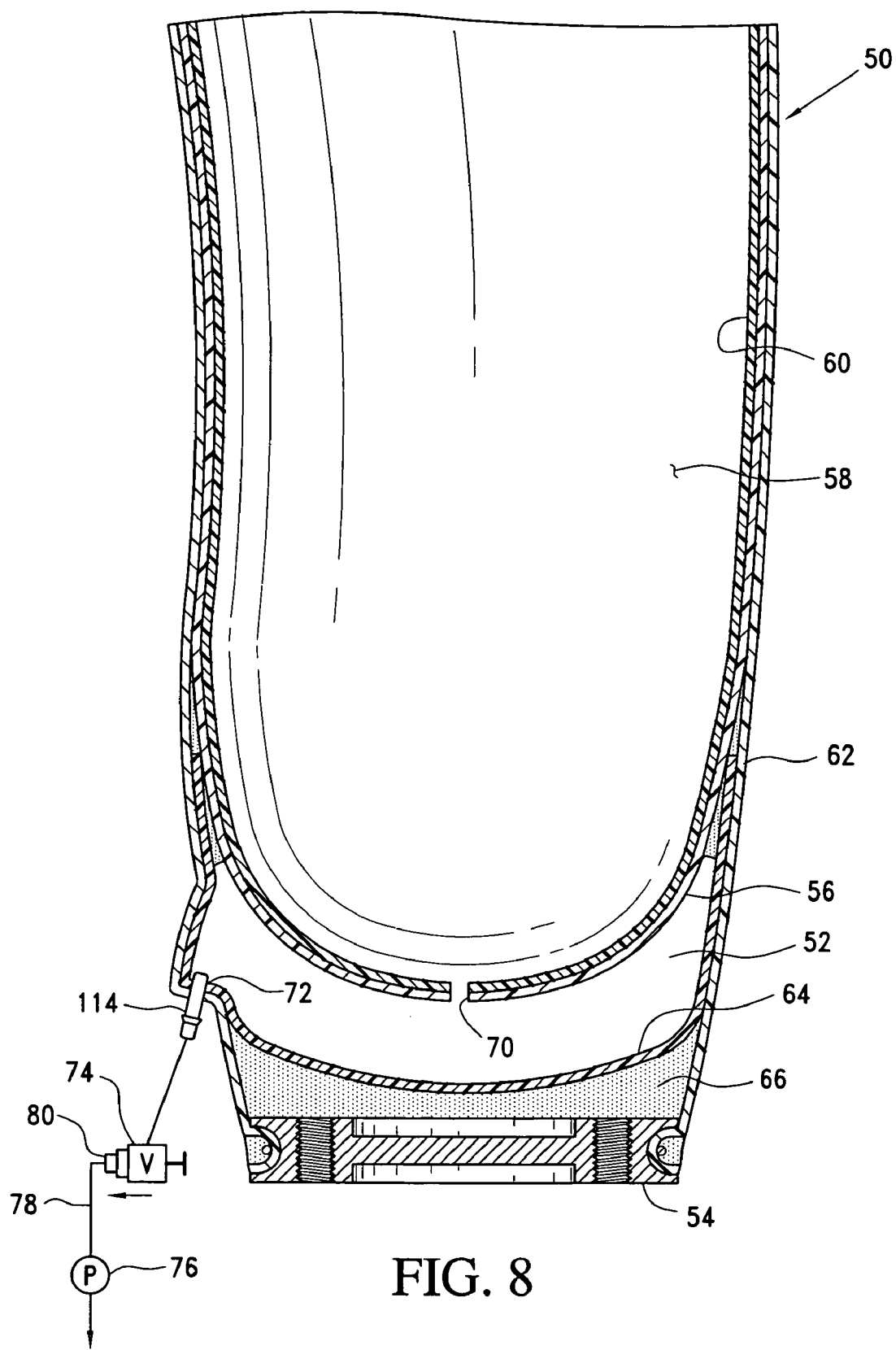
FIG. 8 is a vertical sectional view of a prosthetic socket constructed in accordance with an embodiment of the present invention.

The embodiments of the invention shown in FIGS. 1 and 2 are intended to depict a basic configuration of the invention and to demonstrate the principles underlying the invention. A more practical embodiment of the invention is depicted in FIG. 8 where the prosthetic socket 50 incorporating a self-contained vacuum reservoir chamber 52 is shown integrated with a prosthetic device coupler or adapter 54.

This embodiment of the invention includes an inner wall 56 corresponding to inner wall 12 and 12' shown in FIGS. 1 and 2, the inner wall 56 defining an inner rigid socket adapted to receive the distal end of a residual limb (not shown) and having an inner volume 58 formed and configured to receive a distal end of a residual limb with a sock or liner (with fabric cover or the equivalent) in close fitting relationship therein. The inner wall 56 preferably is provided with a smooth inner lining 60 to facilitate entry of a residual limb and its associated liner within the interior volume 58 of inner wall 56.

The prosthetic socket 50 also includes an outer wall section 62 that is rigid, structural, load bearing and air impervious. Outer wall section 62 in cooperation with the inner wall 56 provides a transition to a prosthetic coupler or adapter 54 of the kind known in the art. Such coupler or adapter enables the prosthetic socket 10 to be secured to a pylon or lower prosthetic device in the case of a leg prosthesis, or other prosthetic device in the case of another limb prosthesis.

In accordance with this embodiment, the vacuum reservoir chamber 52 is partly defined by the exterior wall of the distal end of the inner wall 56 and by a cup-shaped, thin walled spacer member 64 that is firmly secured to the outer wall section 64 along its peripheral regions and is rigidly bonded at its distal region to coupler 54 by structural bonding material 66. The spacer member 64 in this embodiment itself need not constitute a structural element capable of carrying loads between the coupler 54 and the inner wall 56, but rather only needs to cooperate with the outer wall section 62 and the inner wall 56 to define a volume reservoir chamber 52 disposed between the distal end of the inner wall 56 and the inner side of the spacer member 64.

In accordance with this embodiment, the outer wall 62 constitutes the rigid, load bearing structure transferring loads between the coupler 54 and the inner wall 56 while the spacer member 64 is utilized during a manufacturing process used to make the prosthetic socket 50 in an efficient manner using molding, shaping and laminating techniques to be described in connection with FIGS. 3-6 below.

The prosthetic socket 50 includes an aperture 70 serving as a vacuum transfer aperture or port between chamber 52 and the inner volume 58 of inner wall 56 in a manner corresponding to aperture or port 36 of the embodiments shown in FIGS. 1 and 2.

An evacuation port 72 with a selectively operable one-way valve 74 provide communication between the vacuum reservoir chamber 52 and an area outside the chamber via a pump 76 and conduit 78. The conduit 78 may be disconnected from one-way valve 74 via a disconnect element 80 or other appropriate means whereby the chamber 52 is effectively isolated from ambient air pressure.

It will be observed that the outer wall section 62, spacer member 64, structural bonding material 66 and coupler 54 are integrated as a unitary structure adapted to carry loads between a prosthetic device and the inner socket defined by the inner wall 56. In a manner similar to the embodiments illustrated in FIGS. 1 and 2, it is necessary that the walls of the reservoir chamber 52 do not substantially deflect but rather resist deflection to the extent needed to maintain a substantially fixed volume within the chamber during use of the prosthetic socket 50. It is thus important that the residual limb and any associated liner does not protrude into the chamber 52 and it is also important that all loads imposed on the prosthetic socket from a prosthetic device are transmitted through the inner socket defined by the inner wall 56 in a dependable, substantially rigid manner.

Preferably, both the inner wall 56 and the outer wall 62 are formed of carbon fiber reinforced resin material that is structurally strong, resistant to deformation, and impervious to air. This is achieved by extending the carbon fiber reinforced resin material constituting outer wall 62 along a major portion of the inner wall 56 to provide a strongly bonded laminated assembly constituted of carbon fiber reinforced material or an equivalent structural material capable of withstanding loads imposed on the prosthetic socket 50, but which is sufficiently lightweight to be acceptable to amputees in a suction suspension prosthetic socket.

A sealing sleeve (not shown) normally would be used with the prosthetic socket 50 in the same manner as sleeve 46 shown in the embodiment illustrated in FIG. 1, although any other appropriate sealing arrangement could be utilized to isolate the inner volume 58 from atmospheric air leakage at the proximal end of the socket during implementation of the socket.

It is to be understood that the combined assembly of spacer member 64 and outer wall section 62 may be regarded as a single composite structure defining and enclosing the chamber 52. Thus, when reference is made to the "inner side of the outer wall section", such reference may denote the inner surface of the outer wall section 26, 26', or the inner surface of spacer member 64 that functions as an extension of the outer wall section 62 with regard to defining a reservoir chamber 52 in accordance with embodiments of the invention.

Furthermore, reference to a section of the wall of chamber 52 carried by the inner socket externally thereof may refer to either the external wall section 26, 26' in FIGS. 1 and 2, or the combined outer wall section 62 and forming member 64 in the embodiment of the prosthetic socket shown in FIG. 8.

Figure 4:
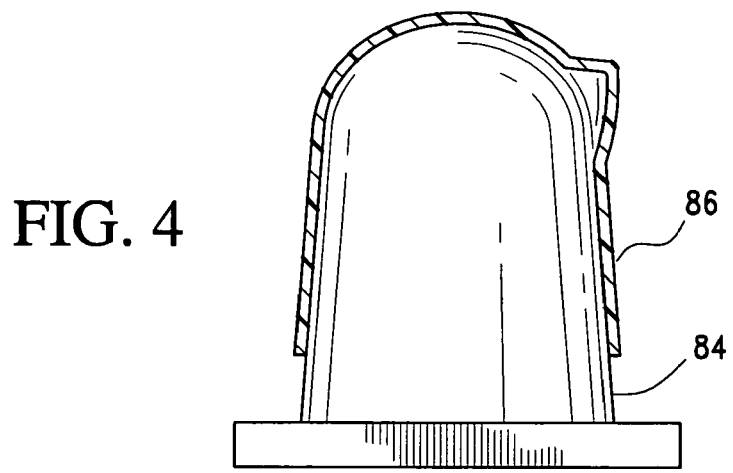

An efficient and economical process for making the prosthetic socket 50 illustrated in FIG. 8 is shown schematically in FIGS. 3-7. It is first desired to thermally form the spacer member 64 from a thermally formable plastic material, preferably PETG (Polyethylene Terephtalate Glycol or polyester copolymer) that is available commercially in clear sheet form and possesses the moldability and strength characteristics suitable for use as the spacer member 64 in the prosthetic socket 50 shown in FIG. 8. PETG sheet ⅛ in. (3.175 mm) available from Piedmont Plastics, Inc. of Charlotte, N.C., U.S.A. has been found to be appropriate for this application A male forming member having an exterior contour corresponding to the desired interior contour of the spacer member 64 is used as a forming core to shape a pre-heated thermo plastic material such as ⅛ in. thick (3.175 mm) PETG simply by a thermal forming process whereby the thermoplastic sheet 86 heated to its softening temperature is draped over the mold 84 and pressed against its outer surface until it closely conforms thereto along the inner surface of the sheet, as shown in FIG. 4. Any desired profile, such as profile 88 used to provide a section for containing the evacuation port 72 may be provided on mold 84 in accordance with the requirements of the spacer member 64.

Figure 5:
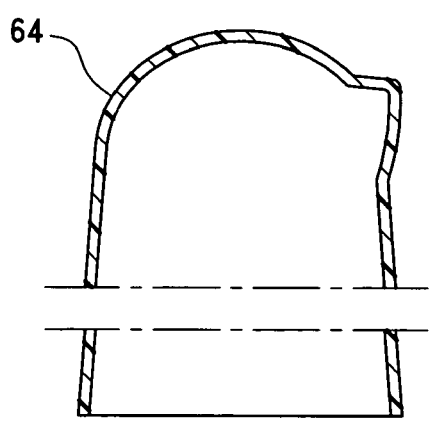
FIG. 5 shows a component of the prosthetic socket according to the present invention.

After cooling, the now relatively rigid sheet 86 is removed from the mold 84 and is cut to an appropriate length as shown in FIG. 5 to leave a cup-shaped spacer member 64 to be used in the process for making the prosthetic socket 50 as will be described below. The mold 84 may be made in, for example, three sizes such as small, medium and large, for installation in various sizes of prosthetic sockets corresponding to socket 50 shown in FIG. 8.

In accordance with another step of the process for making the prosthetic socket 50, a male mold 90 corresponding to the distal end area of a residual limb which has been custom formed in accordance with known procedures is mounted so as to facilitate lay up of another thermoformable heated plastic resin sheet material 60 draped over the outer peripheral surface thereof, such material 60 preferably being constituted of a PETG sheet material on the order of ⅛ inch thick (3.175 mm), although the actual thickness may be varied to suit the prosthetist carrying out the process. The formed sheet 60 constitutes the inner lining of a prosthetic socket to be formed in accordance with the process. The exterior surface of the lining material 60 is roughened to facilitate bonding thereof to the next layer, which is constituted of loose or assembled carbon reinforcement fibers 96 impregnated with a settable resin 104 that will harden and bond the assembly of carbon fibers 96 with the resin to the exterior of the inner lining 60. Impregnation of the carbon fibers 96 with resin may be carried out by vacuum forming using an outer bag 98 tied off at its base by an appropriate cinching element 100 against the exterior of the mold 90, which is provided with a vacuum connection 102 communicating with an external area of the mold 90 between the cinching element 100 and the lower end of the carbon fibers 96. A liquid or semi-liquid hardenable resin 104 is supplied to the top end of the bag 98 in a manner providing a hermetic seal between the interior of the bag 98 and atmosphere, whereby upon application of vacuum to the vacuum connection 102 by a suitable pump, (not illustrated), resin 104 from a suitable supply (not shown) is caused to flow throughout the carbon fibers 96 and to draw the bag 98 firmly against the exterior surface of the carbon fibers and resin matrix against the mold 90 while the resin completely permeates the carbon fibers. When the resin has completely permeated the carbon fibers, the mold is heated sufficiently to heat the resin 104 to its curing temperature in a manner known to those skilled in the art, and subsequently after cooling the bag 98 is removed. Reference is made to U.S. Pat. No. 5,007,937 for a disclosure of impregnating a porous material to form a socket using a vacuum bag technique. A suitable resin 104 could be a suitable epoxy, or acrylic or polyester resin used with carbon fiber reinforcement material known in the prosthetic making art, and available from, for example, Southern Prosthetic Supply of Alpharetta, Ga., U.S.A.

Figure 7:
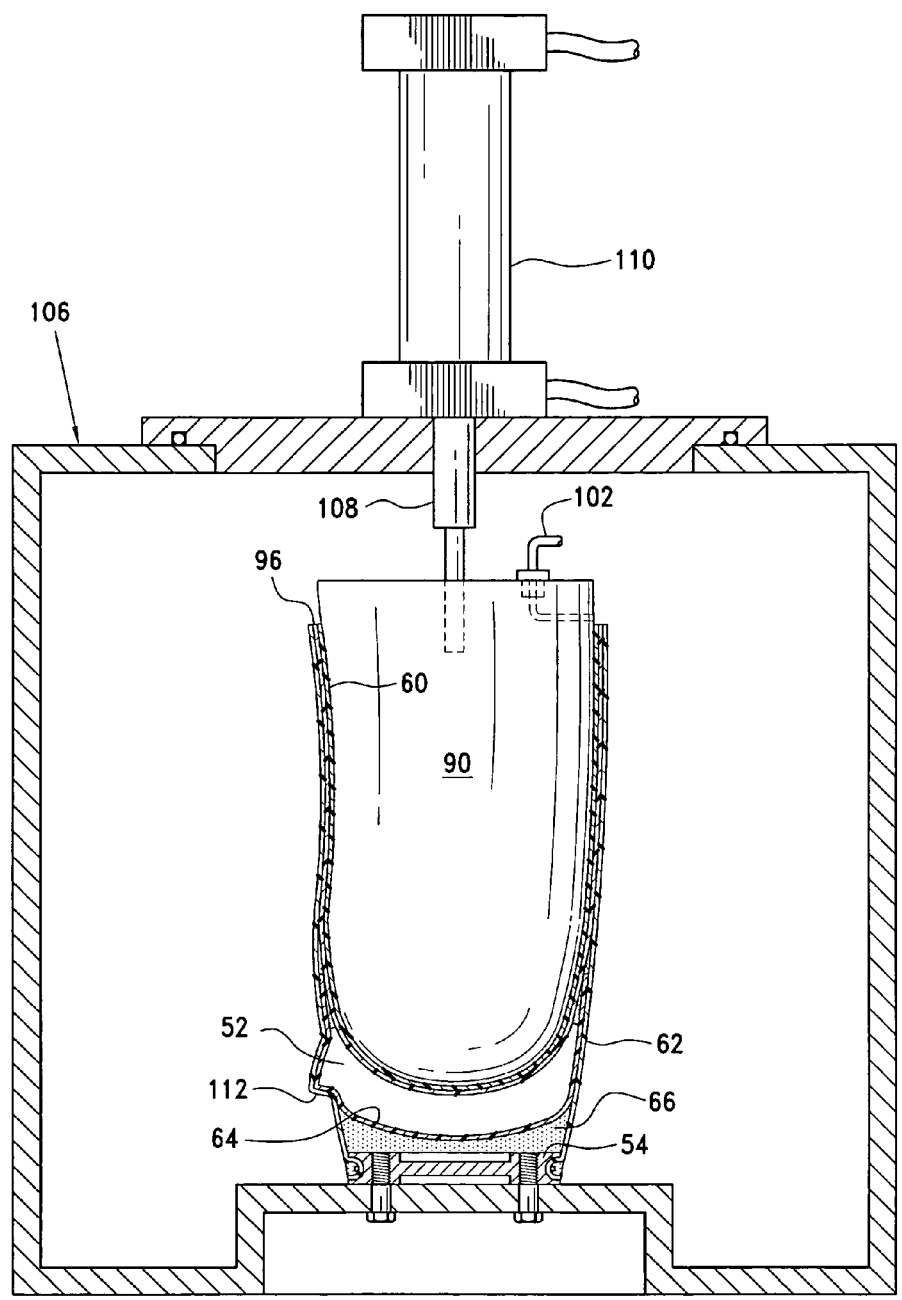
FIG. 7 shows another step in the process for making a prosthetic socket in accordance with the present invention.

Upon removal of the bag 98, the mold mounting is inverted and mounted on an alignment jig 106 as shown in FIG. 7. In the alignment jig 106, the mold 90 is suspended from an appropriate supporting element 108 that may be connected to or which constitutes a part of a hydraulically operated RAM 110 that is arranged to precisely align the mold 90 with the lining 60 having the carbon fiber matrix 96 still mounted thereon in a manner enabling the mold 90 to be moved into proximity to a prosthetic adapter or coupler 54 that is secured at a desired position relative to the mold 90 by a portion of the jig 106. The mold 90 with the lining 60 and carbon fiber matrix 96 is supported initially at a distance from the adapter 54 while the spacer member 64 that has been previously formed in the manner described above is adhesively bonded about its open end to the exterior of the carbon fibers and resin 96 that have been previously cured and hardened. Then, an outer layer of carbon fibers 62 is laid up along the outer surface of the previously molded carbon fibers and resin matrix 96 so as to integrally bond the two layers of carbon fiber together by means of the same resin, for example, used to impregnate the outer layer 62 of the carbon fibers. Preferably, the outer layer of carbon fibers 62 is configured as an annular tube to facilitate the lay up of the fibers along the outer wall of the inner layer of carbon fibers and resin 96 and the resin is impregnated into the outer layer of carbon fibers 62 using the same vacuum bag technique described above with regard to FIG. 6.

Prior to application of the outer layer 62 of carbon fibers, a structural, load bearing resin bonding material is provided between the spacer member 64 and the adapter 54. Preferably, all resins used are formed of the same material, including the resin used to bond the spacer member 64 to the exterior of the inner layer 96 of carbon fibers and resin.

Upon curing and hardening of the outer layer of carbon fibers and resin 62, a reservoir chamber 52 is defined between the exterior distal end of the inner layer of carbon fibers and resin 96 and the inner surface of the spacing member 64. As previously described with regard to FIG. 8, the inner and outer layers of 96, 62 of carbon fiber and resin provides structural strength for transmitting loads between the prosthetic adapter 54 and the inner layer 96 which constitutes an inner rigid load bearing socket member for receiving a residual limb.

The assembly shown in FIG. 7 is then removed from the jig 106 and the mold 90 likewise is separated from the lining 60. The vacuum transfer port 70 is then drilled into the distal end of the inner layer 96 and an evacuation port 72 is drilled into the profile 112 resulting from the previous molding of the spacer member 64 over the profile 88 on mold 84. An appropriate connector or tube element as shown at 114 in FIG. 8 may be provided as a connection to the one-way valve 74 or the one-way valve 74 itself may be integrated with the tube connector 114.

The finished prosthetic socket 50 is illustrated in FIG. 8 which has been previously described.

It is to be understood that carbon fibers are the preferred reinforcement used in making the inner and outer walls of the prosthetic socket as described above. However, any suitable reinforcement material could be used instead of carbon fibers in accordance with generally known technology in the prosthetic socket manufacturing industry. Likewise, the resin to be used with the reinforcement fiber to make the inner and outer walls of the prosthetic socket could be any appropriate resin known in the industry of manufacturing prosthetic sockets.

Additional alternate embodiments of the invention are illustrated schematically in FIGS. 9, 10 and 11. As shown in FIG. 9, a prosthetic adapter 116 could be structurally bonded for an outer wall section 118 formed in the same manner as outer wall sections 26, 26' incorporating a spacer member 120 that is bonded to the external surface of an inner wall (not shown) of a rigid, load bearing inner socket member corresponding to wall 12 and 12' in FIGS. 1 and 2. The spacer member 120, for example, would extend fully in contiguous relationship with the distal portion of the outer wall section 118 and would be bonded in the manner shown in FIG. 8 to the external surface of an inner wall of a prosthetic socket, for example an inner wall corresponding to walls 12 and 12' in FIGS. 1 and 2. With this assembly, a vacuum reservoir chamber would be defined in the volume 122. An appropriate evacuation port (not illustrated) would then be associated with the outer wall section 118 to permit evacuation of air from the volume 122 in the manner described previously in connection with reservoir chambers 34, 34'.

In accordance with FIG. 10, a rigid, structural, load bearing outer wall section 124 formed, for example, of carbon fiber reinforced resin material capable of bearing structural loading between a prosthetic coupler or adapter 126 and an inner wall 128 defining an inner rigid structural load-bearing socket member is bonded to the inner wall 128 as shown at 130 about the distal end of the outer wall section 124. The outer wall section 124 is bonded to the coupler 126 by an appropriate resin providing structural rigidity between the coupler 126 and the outer wall section 124. The outer wall section 124 may extend along the outer peripheral surface of the inner wall 128 to any desired extent as indicated by the hidden lines 132 and is bonded firmly and structurally to the outer peripheral surface of the inner wall 128, which preferably is formed of carbon fiber reinforced resin material.

Bonding of the outer wall 124 to the exterior distal end of the inner wall 128 creates a reservoir chamber 132 that communicates with the inner volume 134 of inner wall 128 adapted to receive the distal end area of a residual limb via a vacuum transfer port 136 in the distal end area of the inner wall 128. An evacuation port 138 provides communication between the vacuum chamber volume 132 and the exterior of the chamber via a one-way valve 140 that may be connected to an appropriate vacuum pump or vacuum source (not shown). A manual vacuum relief 142 may be associated with the valve 140 to enable ventilation of the interior volume 134 of inner wall 128 via transfer port 136. Normally, the one-way valve 140 will retain vacuum or sub-atmospheric pressure within the chamber 132 and inner volume 134 when a residual limb and an associated fabric covered or partially covered liner is fitted with the inner volume 134 of inner wall 128 and an appropriate seal is provided between the inner volume 134 and atmosphere.

In accordance with another embodiment of the invention as shown in FIG. 11, an outer wall section 144 formed of a rigid and structural, load bearing air impermeable material capable of transmitting loads from a prosthetic member through a prosthetic adapter 146 to an inner wall defining an inner socket member 148 that is also formed in a manner heretofore described to define a rigid, structural, load bearing socket member adapted to receive the distal end area of a residual limb. In accordance with this embodiment, the outer wall section 144 completely defines a chamber 150 that is hermetically sealed apart from a vacuum transfer port 152 in communication with an inner volume 154 of inner wall 148 that is intended to receive the distal end portion of a residual limb and an evacuation port 156 corresponding to evacuation ports 38, 72 and 138, including an appropriate one-way valve element 158 arranged to maintain a vacuum established in chamber 150 after a distal end portion of a residual limb and an appropriate sealing device is associated with the inner wall 148.

In all of the preferred embodiments, the evacuation ports 38, 38', 138 and 156 are shown extending through a side wall of the corresponding outer wall section defining a vacuum reservoir chamber. It is also possible to extend the evacuation port through a coupler 54, 116, 126 if desired or to otherwise extend a conduit from the interior of the vacuum chamber 34, 34', 64, 122, 132 and 150 to an area exterior of the vacuum chamber, including an appropriate conduit or channel extending along a section of the prosthetic socket closer to its proximal end.

Preferred embodiments of the inventive subject matter have been described herein for exemplary purposes but it is to be understood that various other structural arrangements and configurations could readily be made by persons skilled in the art without departing from the spirit and scope of the invention, which is defined in the appended claims.

The invention claimed is:

1. A prosthetic socket comprising:
   a rigid, structural, load-bearing, air impervious inner wall in the form of a close ended cup having an open inner wall proximal end and a closed inner wall distal end area, said inner wall defining an inner volume adapted to contain a distal portion of a residual limb, and said inner wall proximal end adapted to receive a distal portion of a residual limb to be located within said inner volume;
   a generally continuously cup-shaped, rigid, air impervious structural, load-bearing outer wall section having an outer wall section proximal end and a closed outer wall section distal end area;

a hermetic sealing connection between an outer side of said inner wall and an inner side of said outer wall section located proximally relative to said closed outer wall section distal end area;

a vacuum reservoir chamber defined between an outer side of said inner wall and an inner side of said outer wall section, said chamber hermetically sealed along said hermetic sealing connection, the chamber defining a constant and fixed volume;

at least one aperture in said inner wall communicating the inner volume of said inner wall with said chamber, the aperture being substantially smaller in cross-section than the closed inner wall distal end area;

a port communicating said chamber with an area external of said outer wall section;

whereby a partial vacuum may be established within said chamber via said port when a residual limb is contained in said inner volume of said inner wall and said partial vacuum may be communicated to said inner volume of said inner wall to effect a vacuum suspension of the prosthetic socket on the residual limb via said at least one aperture in said inner wall.

2. The prosthetic socket as claimed in claim 1, wherein said chamber is disposed adjacent said closed outer wall section distal end area.

3. The prosthetic socket as claimed in claim 1, wherein said closed outer wall section distal end area comprises a prosthetic adapter.

4. The prosthetic socket as claimed in claim 1, wherein said inner wall comprises a reinforced resin material.

5. The prosthetic socket as claimed in claim 4, wherein said inner wall comprises carbon fiber reinforcement.

6. The prosthetic socket as claimed in claim 1, wherein said inner wall and said outer wall section comprise reinforced resin material.

7. The prosthetic socket as claimed in claim 6, wherein said inner wall and outer wall section comprise carbon fiber reinforcement.

8. The prosthetic socket as claimed in claim 1, wherein said chamber is hermetically sealed other than said aperture in said inner wall and said port.

9. The prosthetic socket as claimed in claim 1, wherein said outer wall section comprises a laminated structure comprising an outer rigid, structural layer defining one part of said outer wall closed distal end area, and an inner air impervious layer coextending at least in part with said outer layer along the outer wall closed distal end area of said outer wall section, said chamber disposed between an inner side of said inner layer and an outer side of said inner wall; and said hermetic sealing connection disposed at least in part between an inner side of said inner layer and an outer side of said inner wall.

10. The prosthetic socket as claimed in claim 9, said outer wall section including a prosthetic adapter disposed at the outer wall section distal end area.

11. The prosthetic socket as claimed in claim 10, including a rigid structural bonding material between said prosthetic adapter and said inner layer.

12. The prosthetic socket as claimed in claim 9, said port extending through said inner layer and said outer, rigid structural layer.

13. The prosthetic socket as claimed in claim 9, said outer rigid structural layer of said outer wall section and said inner wall comprising a reinforced resin material.

14. The prosthetic socket as claimed in claim 13, said outer rigid structural layer of said outer wall section and said inner wall comprising carbon fiber reinforcement.

15. The prosthetic socket as claimed in claim 9, said outer rigid structural layer of said outer wall section including a proximal area extending over and enclosing a portion of said inner wall and being bonded to an external surface of said inner wall along an area proximally located relative to said hermetic sealing connection.

16. The prosthetic socket as claimed in claim 15, said outer rigid structural layer of said outer wall section and said inner wall comprising carbon fiber reinforced resin material.

17. The prosthetic socket as claimed in claim 16, said inner air impervious layer comprising a molded thermoplastic continuous resin sheet material.

18. The prosthetic socket as claimed in claim 1, said port extending through the outer wall section.

19. The prosthetic socket as claimed in claim 1, said inner wall comprising a laminated assembly including a smooth inner layer defining the inner wall inner volume, and a carbon fiber reinforced resin outer layer bonded to an outer surface of said inner layer, said inner layer comprising a continuous molded thermoplastic sheet plastic material.

20. A prosthetic socket adapted for vacuum suspension of a prosthetic device relative to a residual limb, said socket comprising:

a rigid, structural, load-bearing, cup-shaped socket member defining a substantially closed distal end, an inner volume terminating distally at said distal end for receiving a distal portion of a residual limb, and an open proximal end arranged to admit a distal portion of a residual limb into the inner volume;

a vacuum reservoir chamber located externally of and carried by said socket member, the vacuum chamber defining a constant and fixed volume, said vacuum reservoir chamber defined at least in part by a rigid chamber wall section hermetically sealed and directly attached to an outer side wall of the socket member;

said chamber wall section being rigid and inflexible so as to avoid deflection when the pressure in the reservoir chamber varies during implementation of the prosthetic socket;

an evacuation port in communication with said reservoir chamber for enabling establishment of a partial vacuum within said reservoir chamber; and at least one vacuum transfer port defined by and extending through a thickness of the socket member, and communicating said reservoir chamber with said inner volume of said socket member for enabling transfer of a partial vacuum within said reservoir chamber into said inner volume, each of said at least one vacuum transfer port being located at the distal end of the socket member and being substantially smaller in cross section than said distal end which is closed except for said at least one vacuum transfer port.

21. The prosthetic socket as claimed in claim 20, said reservoir chamber defined by said chamber wall section and the exterior of said socket member, and located between said chamber wall section and the exterior of said socket member.

22. The prosthetic socket as claimed in claim 21, said reservoir chamber disposed adjacent and outside of the substantially closed distal end of said socket member.

23. The prosthetic socket as claimed in claim 20, including a prosthetic adapter associated with said chamber wall section, said chamber wall section being structurally sufficiently rigid to carry operational loads between said socket member and said prosthetic adapter during implementation of the prosthetic socket;

said chamber wall section comprising a structural load-bearing portion of the prosthetic socket, and arranged to transfer operational loads between the socket member and a prosthetic device via said prosthetic adapter.

24. The prosthetic socket as claimed in claim 23, said chamber wall section and said socket member comprising a carbon reinforced resin material.

25. The prosthetic socket as claimed in claim 24, said prosthetic adapter comprising a metal material.

26. The prosthetic socket as claimed in claim 20, said evacuation port communicating to an area outside said reservoir chamber via a one-way check valve operational so as to selectively permit evacuation of air out of the reservoir chamber but not ingress of air into the reservoir chamber.

27. The prosthetic socket as claimed in claim 20, said chamber wall section extending partially over an outer surface of said socket member and secured thereto by a bonding agent;

said chamber wall section including a distal end area and a prosthetic adapter comprising a portion of the distal end of said chamber wall section;

said chamber wall section having sufficient structural strength to enable the chamber wall section to transfer operational loads between said socket member and said prosthetic adapter during implementation of the prosthetic socket.

28. The prosthetic socket as claimed in claim 27, said socket member and said chamber wall section formed of carbon fiber reinforced resin material, said resin material also comprising said bonding agent.

29. A prosthetic socket comprising:

a rigid, structural, load-bearing, air impervious inner wall in the form of a close ended cup having an open inner wall proximal end and a closed inner wall distal end area, said inner wall defining an inner volume adapted to contain a distal portion of a residual limb, and said inner wall proximal end adapted to receive a distal portion of a residual limb to be located within said inner volume;

a generally continuously cup-shaped, rigid, air impervious structural, load-bearing outer wall section having an outer wall section proximal end and a closed outer wall section distal end area;

a hermetic sealing connection between an outer side of said inner wall and an inner side of said outer wall section located proximally relative to said closed outer wall section distal end area;

a vacuum reservoir chamber defined between an outer side of said inner wall and an inner side of said outer wall section, said chamber hermetically sealed along said hermetic sealing connection, the chamber defining a constant and fixed volume;

at least one aperture in said inner wall communicating the inner volume of said inner wall with said chamber, the aperture being substantially smaller in cross-section than the closed inner wall distal end area;

a port communicating said chamber with an area external of said outer wall section, said port communicating to an area outside the outer wall section via a one-way check valve operational so as to selectively permit evacuation of air out of the chamber but not ingress of air into the chamber;

whereby a partial vacuum may be established within said chamber via said port when a residual limb is contained in said inner volume of said inner wall and said partial vacuum may be communicated to said inner volume of said inner wall to effect a vacuum suspension of the prosthetic socket on the residual limb via said at least one aperture in said inner wall.

* * * * *